United States Patent
Schönrock et al.

(10) Patent No.: US 11,162,905 B2
(45) Date of Patent: Nov. 2, 2021

(54) METHOD FOR DETERMINING THE QUALITY AND/OR COMPOSITION OF MILK, IN PARTICULAR DURING A MILKING PROCESS

(71) Applicant: GEA Farm Technologies GmbH, Bönen (DE)

(72) Inventors: Karsten Schönrock, Hagen (DE); Marek Krasutzki, Telgte (DE); Sascha Bieletzki, Bönen (DE); Reinhard Balkenhol, Paderborn (DE)

(73) Assignee: GEA Farm Technologies GmbH, Bönen (DE)

( * ) Notice: Subject to any disclaimer, the term of this patent is extended or adjusted under 35 U.S.C. 154(b) by 312 days.

(21) Appl. No.: 15/467,694

(22) Filed: Mar. 23, 2017

(65) Prior Publication Data

US 2017/0191943 A1 Jul. 6, 2017

Related U.S. Application Data

(63) Continuation of application No. 14/385,482, filed as application No. PCT/EP2013/055521 on Mar. 18, 2013, now abandoned.

(30) Foreign Application Priority Data

Mar. 16, 2012 (DE) ...................... 10 2012 005 205.7

(51) Int. Cl.
*G01N 21/84* (2006.01)
*G01N 33/04* (2006.01)
(Continued)

(52) U.S. Cl.
CPC ................ *G01N 21/84* (2013.01); *A01J 5/01* (2013.01); *A01J 5/0135* (2013.01);
(Continued)

(58) Field of Classification Search
CPC .......... A01J 5/01; A01J 5/0135; G01N 33/04; G01N 21/84
See application file for complete search history.

(56) References Cited

U.S. PATENT DOCUMENTS 5,116,119 A 5/1992 Brayer
6,493,071 B2 * 12/2002 van den Berg ........... A01J 5/00
119/14.08
(Continued)

FOREIGN PATENT DOCUMENTS

EP 1000535 5/2000
EP 1287737 A2 3/2003
(Continued)

OTHER PUBLICATIONS

International Search Report for International Application No. PCT/EP2013/05521 dated Jun. 18, 2013.
(Continued)

*Primary Examiner* — Violeta A Prieto
(74) *Attorney, Agent, or Firm* — Smith Law Office; Jeffry W. Smith

(57) ABSTRACT

A method is proposed for ascertaining the quality and/or the composition of milk, in particular during a milking operation, in which the fill level of the milk in a chamber is determined. After the fill level of the milk in the chamber has been determined, the milk is irradiated using at least one radiation of a predefined wavelength. The intensity of the reflected radiation is measured. The fill level and the intensity of the reflected radiation represent a value pair. Characteristic values are stored in a memory. A characteristic value is assigned to the ascertained value pair. A statement about the quality and/or the composition of the milk can be made from the characteristic value thus ascertained.

29 Claims, 8 Drawing Sheets

(51) Int. Cl.
*A01J 5/01* (2006.01)
*A01J 5/013* (2006.01)
*G01F 23/292* (2006.01)

(52) U.S. Cl.
CPC ........... *G01F 23/292* (2013.01); *G01N 33/04* (2013.01); *G01N 2201/0621* (2013.01); *G01N 2201/0696* (2013.01); *G01N 2201/06113* (2013.01)

(56) References Cited

U.S. PATENT DOCUMENTS

| | | | |
|---|---|---|---|
| 8,072,594 B1* | 12/2011 | McMahon | G01F 23/2927 356/246 |
| 9,668,452 B2* | 6/2017 | Buchholz | A47J 31/4485 |
| 2002/0054831 A1 | 5/2002 | Berg et al. | |
| 2003/0098969 A1* | 5/2003 | Katz | G01N 21/31 356/73 |
| 2005/0034518 A1* | 2/2005 | Wamhof | G01F 1/708 73/227 |
| 2010/0021177 A1 | 1/2010 | Osterberg | |
| 2010/0071626 A1* | 3/2010 | Hoey | A01J 5/0133 119/14.02 |
| 2010/0210022 A1* | 8/2010 | Madura | C12Q 1/6883 436/86 |
| 2010/0273273 A1 | 10/2010 | Cross et al. | |
| 2015/0020738 A1* | 1/2015 | Krone | A01J 5/007 119/14.04 |
| 2015/0146194 A1* | 5/2015 | Schonrock | A01J 5/01 356/73 |
| 2018/0361040 A1* | 12/2018 | O'Toole | G16H 40/63 |
| 2019/0242816 A1* | 8/2019 | Conner | G01N 33/04 |

FOREIGN PATENT DOCUMENTS

| | | |
|---|---|---|
| EP | 2036470 A1 | 3/2009 |
| GB | 2352033 A | 1/2001 |
| WO | 2001019170 A1 | 3/2001 |
| WO | 2001056369 A1 | 8/2001 |
| WO | 2002084260 A1 | 10/2002 |
| WO | 2005093387 A1 | 10/2005 |
| WO | 2006028706 A1 | 3/2006 |

OTHER PUBLICATIONS

German Office Action in corresponding application No. 10 2012 005 205.7 dated Mar. 1, 2013.
International Report on Patentability for International Application No. PCT/EP2013/05521 dated Sep. 29, 2014.

* cited by examiner

METHOD FOR DETERMINING THE QUALITY AND/OR COMPOSITION OF MILK, IN PARTICULAR DURING A MILKING PROCESS

CROSS REFERENCE TO RELATED APPLICATIONS

This application is a continuation of U.S. application Ser. No. 14/385,482, filed Sep. 15, 2014, which is a national phase application under 35 U.S.C. § 371 of PCT International Application No. PCT/EP2013/055521, filed Mar. 18, 2013, which claims priority to German Application No. 10 2012 005 205.7 filed Mar. 16, 2012, the disclosures of which are incorporated by reference herein.

FIELD AND BACKGROUND OF THE INVENTION

The invention relates to a method for determining the quality of milk.

Raw milk is a significant food and an important raw material for the food industry. For the protection of the consumer, for the technical processing capability, and for market control, raw milk must correspond to specific national and international quality requirements. For example, reference is made for this purpose to the regulation about requirements on hygiene during the production, treatment, and marketing of certain foods of animal origin (animal foods—hygiene regulation—animal LMHV) or the regulation (EC) No. 852/2004 of the European Parliament and of the Council of Apr. 29, 2004 on food hygiene.

In milking devices and methods in general and in particular in automatic and automated milking using semiautomatic and also fully automatic milking systems, expanded functions are playing an increasingly larger role. In particular, ensuring quality standards of the milk, in particular also the testing for obviously altered milk, is in the foreground. Obviously altered milk means that the milk is contaminated by blood, pus, or by flakes, i.e., has been noticeably altered in an undesirable manner in the appearance with respect to color, odor, or consistency. Various methods are known to determine the obviousness. Some methods use conductance measurements or density measurements or screens to determine the content of flakes in the milk. Others detect obvious changes with respect to color changes of the milk.

A method for the qualitative characterization of milk during a milking operation is known from EP 1 287 737 A2. For this purpose, at least one acoustic transmission signal is emitted, which is influenced by the milk. A reception signal is recorded. At least one characteristic value, which is capable of characterizing the quality of the milk, is derived from the recorded reception signal. The quality of the milk can already be determined during the milking by this method. In this way, for example, only the milk which is qualitatively suitable for further processing is conducted into a collection container. This reduces the risk of contamination of the milk in the collection container by milk of an inadequate quality grade.

A method for the optical characterization of milk using an optical system is known from WO 2002/084260. Firstly, the optical system is calibrated in at least one frequency. Subsequently, at least one optical spectrum of the milk of at least one frequency is recorded, upon which the obtained spectrum is imaged with the aid of a first image in a color space of at least one color vector. Then, at least one color vector is imaged with the aid of a second image of a feature space on a feature vector. By way of this method, the milk is characterized in a contactless manner, in real time, and in the continuous flow method. The optical transmission function of the optical system is established by the calibration, so that it can be calculated out later from the optical spectra recorded using milk. For example, the offset comparison and an automatic calibration using reference values are performed for the crude values of the sensor. After this step, the individual crude values are also considered in isolation per se.

EP 1 000 535 also relates to ascertaining the quality of milk. For this purpose, a method is proposed, using which a source successively irradiates the milk using radiation of different wavelengths. A receiver measures, during at least a part of the time in which the source is turned on, the intensity of the reflected radiation over a period of time. The values of the radiation intensity measured in this manner are stored in a memory. The values are compared to one another and to earlier values, which were recorded during an earlier measurement. The result of this comparison operation is displayed. In the case of such a method, the problem exists that the values of the radiation intensity of the milk vary strongly depending on the amount of ambient light. It is therefore proposed that the source be turned off during a measurement, because the receiver measures the intensity of the reflected radiation over a period of time during at least a part of the time in which the source is turned off. The values of the radiation values measured in this manner are stored as background values in a memory. The background values are integrated into the values which were obtained during the time in which the source was turned on. The values corrected by the background values are stored in a memory. A correction of the radiation intensity which is measured and in which the sources are turned on is made possible by this procedure.

A device for ascertaining physical anomalies in milk is known from WO 01/056369. The device has at least one light source to irradiate milk and/or milk samples using light of red and/or green and/or blue color. At least one light sensor is provided for measuring the intensity of light which is reflected and/or scattered and/or transmitted by the milk. The measurement data are processed by means of a computer. The computer is programmed for this purpose so as to select on the basis of a comparison of the values derived from the measured light intensities to reference values or by way of multiple diagnoses for the anomalies in the milk from a plurality of stored possible diagnoses.

SUMMARY OF THE INVENTION

Proceeding therefrom, the present invention is based on the object of specifying an improved method for determining the quality of the milk.

This object is achieved by a method for ascertaining the quality and/or the composition of milk according to the features of patent claim 1. Further advantageous embodiments of the invention are specified in the patent claims formulated as dependent. The individual features set forth in the patent claims can be combined in any desired technologically reasonable manner with one another and can be supplemented by explanatory facts from the description, wherein further embodiment variants of the invention are disclosed.

According to the method according to the invention for ascertaining the quality and/or the composition of milk, in particular during a milking operation, it is proposed that the fill level of the milk in a chamber is determined. The chamber can be formed by a section of a milk hose or the like, so that the milk flows through the chamber. At the point in time of the measurement or determination of the quality of the milk, the fill level, i.e., the liquid level of the milk in the chamber, is determined. Alternatively or additionally, the chamber can be implemented inside a line. The chamber can have a predefined volume, into which the milk flows during the flow through the line. It is also possible that the chamber is arranged on a bypass line. A sample of the milk can optionally be drawn and it can be studied in a chamber. Flake detection, and a determination of urea, lactose, and/or fat in the milk can be achieved by the method according to the invention. Furthermore, a determination of the somatic cells in the milk can also be carried out by means of the method.

However, it is advantageous if during the milking operation, the chamber is formed by the section of a line system of the milking system, so that the quality and/or the composition of the milk is/are already ascertained during the milking operation.

After the fill level of the milk in a chamber has been determined, the milk is irradiated using at least one radiation of a predefined wavelength. The intensity of the reflected radiation is measured. The fill level and the intensity of the reflected radiation form a value pair. Characteristic values are stored in a memory. A characteristic value is assigned to the ascertained value pair. A statement about the quality and/or the composition of the milk can be made from the characteristic value thus ascertained.

A method is preferred in which the fill level of the milk in the chamber is measured in a contactless manner. An embodiment of the method is particularly preferred in this case in which the milk is irradiated using red light and the fill level of the milk in the chamber is determined from the intensity of the reflected red light.

According to a further advantageous embodiment of the method, it is proposed that the predefined wavelength of the light corresponds to the wavelength of the green or blue light. A statement as to whether and in what concentration hemoglobin is located in the milk can be made from the intensity of the reflected green light.

The intensity of the reflected radiation of the blue light can be used for the purpose of obtaining items of information about how high the aqueous proportion in the milk is. The aqueous proportion of the milk can be a significant indication that an *E. coli* infection is present.

The intensity of the reflected blue light can also be used as a monitoring signal for a cleaning of the chamber to be carried out. The chamber is cleaned by means of water or a liquid containing water, a statement can thus be made from the intensity of the reflected parts of the blue light as to whether the cleaning operation is running properly. Since the cleaning operation or the chamber can represent a part of a line system of the milking facility, monitoring of the cleaning of the line system of the milking system can also be achieved.

The milk located in the chamber can be irradiated using white light for a predefined duration. A correspondingly implemented receiver, which has at least one optical filter, for example, receives the reflected light and delivers corresponding signals to a controller. Receivers and/or filters can be provided which operate selectively, so that only reflected light of predefined wavelengths is analyzed.

The receiver or the receivers can successively or simultaneously relay the measurement signals corresponding to the selected wavelengths of the light to a controller. According to an advantageous embodiment of the method, it is proposed that the milk is irradiated using pulsing radiation. The time multiplexing method can be used for this purpose. The radiation can be white light. The milk is preferably successively irradiated using one or different wavelengths of the light. In this way, discrete responses of the sensor about the intensity of the reflected light in specific wavelengths can be obtained.

The characteristic values can be stored in a characteristic curve map or also as a lookup table in a memory. It is also possible to provide a mathematical relationship, by means of which, on the basis of the ascertained intensity of the reflection of the light and the height of the fill level in the chamber, an item of information is obtained about the proportion of a specific component in the milk.

To increase the efficiency of the method for ascertaining the quality and/or the composition of the milk, it is proposed that a milk stream, in particular a minimum milk stream, which flows through the chamber or into the chamber, is detected. The determination of the fill level in the chamber is only performed thereafter. The detection of the milk stream can be performed, for example, by means of a conductance sensor. The conductance sensor can be arranged downstream from the chamber, for example. In this way, it is also ensured that when the conductance sensor detects the presence of the milk, it has also at least partially flowed through the chamber. Instead of a conductance sensor, other sensors which detect the flow of the milk can also be used.

According to the method according to the invention, the milk in the chamber is irradiated with at least one radiation of a predefined wavelength. A method in which the radiation is a monochromatic radiation is preferred in this case. In this way, a greater reliability with respect to the possible statement about the composition and/or the quality of the milk is also achieved, since monochromatic radiation has a clearly defined wavelength.

Alternatively or additionally to the determination of the fill level by means of red light, the fill level can also be determined capacitively or inductively.

To reduce the analysis expenditure, according to a further advantageous idea, it can be proposed that the fill level in the chamber is predefined. It is established whether the fill level which was predefined is reached. This can be performed capacitively or inductively. Resistance measurements can also be made. For example, an electrode pair, which is wetted by the milk, can be arranged in the upper region of the chamber. If such wetting is present, a circuit can be closed, which is an indication of reaching a predefined fill level. Then, for example, the information about the proportion or the concentration of a component in the milk can also be derived from the knowledge of the fill level and the intensity of the reflected radiation.

To carry out the method, it is proposed that at least one sensor having at least one light source and at least one receiver is provided, wherein the sensor is calibrated to a herd-specific or animal-individual white of the milk. The "white" of the milk is dependent on the fat content in the milk. The fat content in the milk is animal-individual. If an animal identification system is provided, the information about the animal-individual white of the milk can be stored in a herd management system. If the animal is milked, it is thus firstly identified. Data which are provided to the system then follow from the identification of the animal. A change of the milk or its composition can also be derived on the basis of the animal-individual white. In any case, the animal-individual white of the milk can be stored and used for the calibration of the system for a following milking operation of this animal. Instead of the use of the animal-individual white of the milk, a herd-specific white of the milk can also be provided. The herd-specific white of the milk follows from the values of the single animal-individual color of the milk.

Conclusions on following actions or treatments of the animal can be derived from the ascertained characteristic values, or via at least one characteristic value. For example, if it is established that the characteristic value exceeds a predefined limiting value, for example, the milk can be diverted into a tank for unusable milk, to ensure that, for example, milk having a high blood content does not enter a tank which contains usable milk. The health status of the herd can also be concluded from the characteristic values of the animals. If significant characteristic values are present in specific ranges, this can be an indication for measures to derive or carry out the health of the animals and therefore also of the entire herd.

The measurement of the milk can be performed individually by udder quarter in the case of cows. This is not absolutely necessary, but is advantageous.

Insofar as the above statements relate to milking a cow, this does not represent a restriction. The animals to be milked can be cows, goats, sheep, dromedaries, mares, or yaks and further types of animals.

Further advantages and details of the invention will be explained on the basis of the exemplary embodiment shown in the drawing, without the subject matter of the invention being restricted to this concrete exemplary embodiment.

DETAILED DESCRIPTION OF THE DRAWINGS

Figure 1:
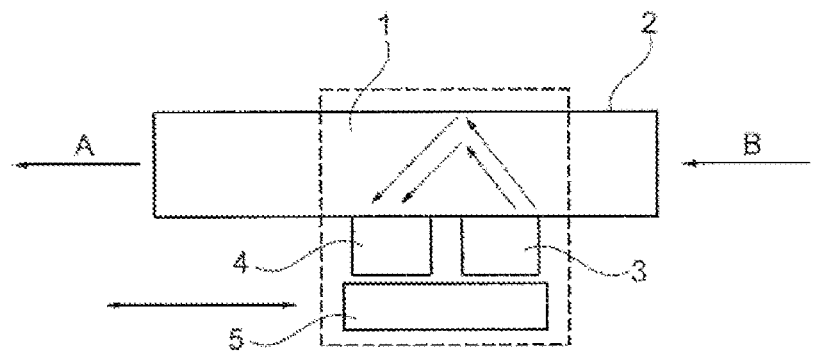
FIG. 1: schematically shows a device for ascertaining the quality and/or the composition of milk.

FIG. 1 schematically shows a device for ascertaining the quality and/or the composition of milk. The device comprises a chamber 1. The chamber 1 is formed by a line section 2. The line section 2 is preferably made of glass. The line section 2 can also be formed from another material, wherein it must be ensured that the radiation can enter and exit the chamber. The flow direction of milk, which is obtained during a milking operation, is identified with the arrows A and B. The milk flows through the chamber 1 in the line section 2. The chamber 1 is preferably implemented so that light influences from the environment cannot enter the chamber 1. If light influences from the environment should be present, these are to be compensated for and/or taken into consideration by appropriate optical filters and/or measurement with the light source turned off.

A light source is identified with the reference sign 3. The light source emits at least one radiation of a predefined wavelength. The light source can be a light-emitting diode (LED) or a laser diode. The light source can also have multiple individual light sources, by means of which the milk located in the chamber is irradiated using red, green, and/or blue light. It is also possible that the light source emits white light and individual spectral components of the reflected light are individually determined on the receiver side. At least one optical filter can be provided for this purpose.

The light entering the chamber is at least partially reflected. The course of the light beams is schematically indicated in FIG. 1. A receiver 4 ascertains the spectral color components (red, green, blue) reflected from the milk periodically and/or simultaneously. Both the light source and also the receiver are connected to a controller 5. By means of the controller 5, the light source 3 can be activated, in particular the measurement operation can be triggered. The controller 5 can be connected to further components of a milking system. In particular, the controller can be connected to a component, for example, by means of which the presence of milk in the line is verified. The component transmits a signal to the controller 5, by which a measurement operation can be triggered. This component can also be used for the purpose of terminating the measurement operation or a plurality of successive measurement operations when no milk is present in the milk line.

The controller can also receive a signal from a cleaning unit, so that a cleaning operation can also be monitored by means of the device, as explained hereafter.

The controller preferably has a memory, in which the characteristic values are stored. A characteristic value is ascertained for the value pair fill level and intensity of the reflected radiation. This characteristic value can be compared to a reference value, so that a statement can be made about the composition and/or quality of the milk.

The measurement is preferably performed periodically, so that multiple measured values can be obtained during one milking operation. The measurement can also be performed simultaneously, and specifically in the meaning that multiple spectral components of the light reflected from the milk are used to ascertain the characteristic value.

The red and green spectral components of the light acquired by the receiver are used to determine the blood content.

Figure 2:
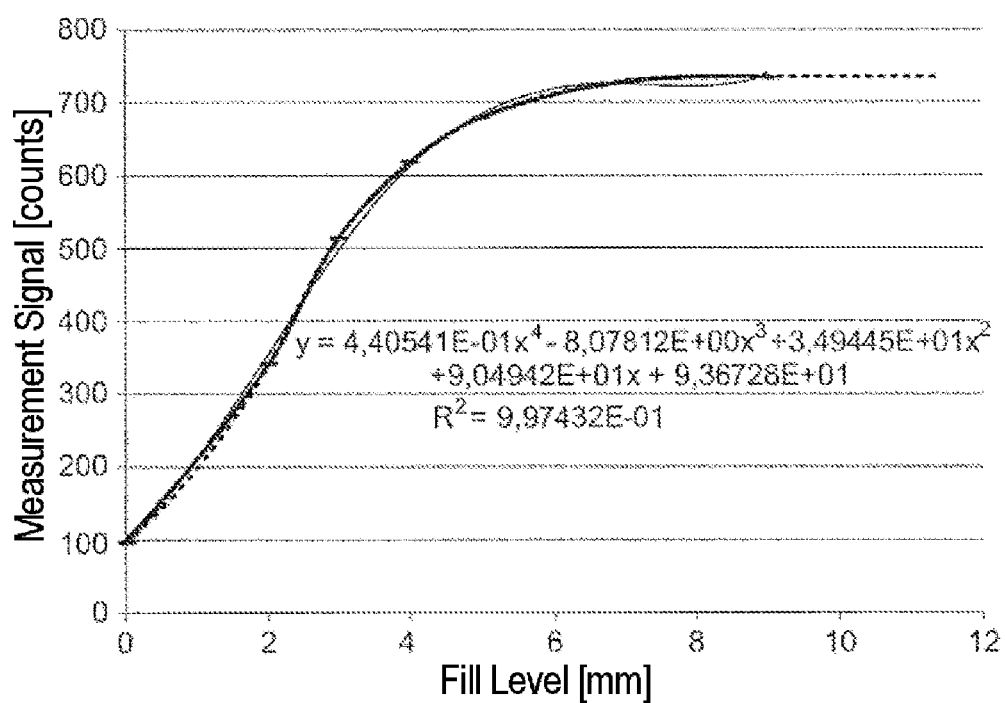
FIG. 2: shows the level of a measurement signal in dependence on the fill level and amaranth concentration in the milk in the case of an analysis of the light intensity of the red light.

FIG. 2 shows the course of the measured values of the red component in dependence on the fill level. The red spectral component which the receiver ascertains provides conclusions about the fill level of the milk in the chamber. The illustration in FIG. 2 shows that the fill level is essentially independent of a concentration of amaranth in the milk. These data can be analytically described, so that a mathematical relationship between the values of the receiver signal and the fill level in the chamber can be provided. Amaranth is a red colorant, which is readily soluble in milk and served as a good substitute for blood in the milk in the experiments. A direct correlation exists between an amaranth concentration and a hemoglobin concentration in milk, so that a statement about the corresponding hemoglobin concentration in the milk and therefore also about blood in the milk can be made from the knowledge of the amaranth concentration in the milk. Therefore, reference is made to hemoglobin hereafter.

The fill level of the milk in the chamber 1 is determined from the intensity of the red light reflected from the milk. If the milk located in the chamber 1 is irradiated using red light, the fill level of the milk in the chamber can thus be determined from the reflected light quantity. It is also possible to analyze the red spectral component of the reflected light if the light source is broadband. The knowledge about the fill level in the chamber 1 is produced from the measurement result.

A statement about the hemoglobin concentration in milk (μmol/L; μmol per liter) can be ascertained by means of the green spectral component and the known fill level of the milk in the chamber.

Figure 3:
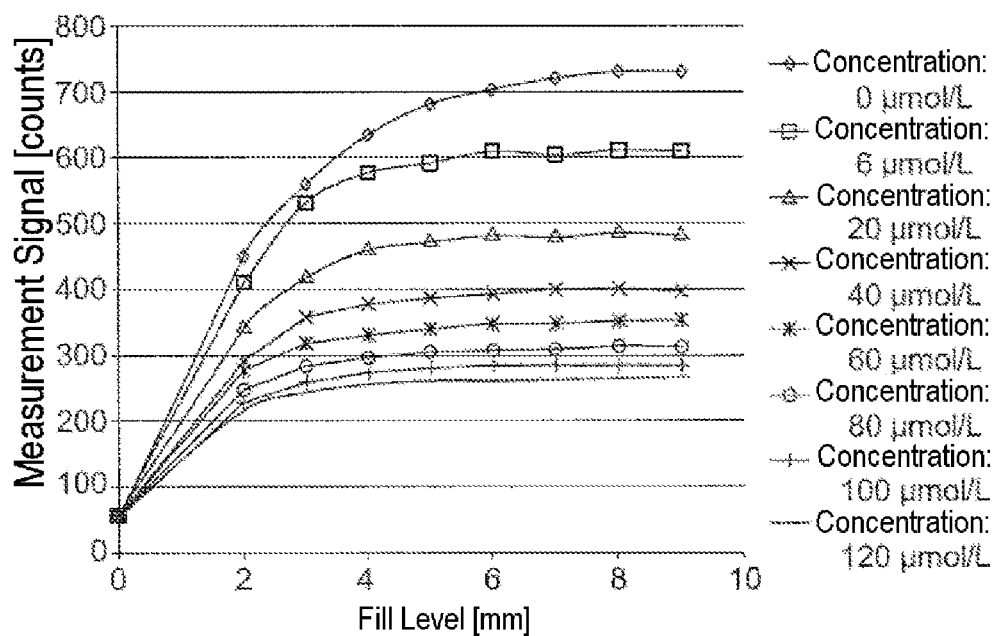
FIG. 3: shows a diagram and the dependence of the measurement signal on the fill level and the amaranth concentration in milk in the case of the analysis of the green light.

FIG. 3 shows the relationship between the green spectral component, the fill level, and the hemoglobin concentration in the milk resulting therefrom. A characteristic value can be ascertained from stored characteristic values from the value pair fill level and intensity of the reflected radiation. The courses, as shown in FIG. 3, can be stored. The possibility also exists that the characteristic values are stored in the form of a table, in particular a lookup table. Alternatively or additionally, the fill level and the intensity of the reflected radiation can be used as parameters in a mathematical relationship for the determination of a characteristic value.

From the illustration in FIG. 3 it follows, for example, that in the case of a fill level of the chamber of 4 mm and a measurement signal of the receiver of approximately 300 counts, a hemoglobin concentration of 80 μmol/L is present in the milk.

The operating mode of the device for ascertaining the quality and/or the composition of the milk has been described on the basis of the measurement chamber 1, through which the milk flows. If the measurement chamber has a constant, predefined measurement volume, it is only necessary to analyze the green spectral component of the light to arrive at the desired result.

The measurement can be carried out as a multiplex measurement. The light source or light sources preferably emit monochromatic light. If the light source or light sources emit a broadband light, the receiver is thus equipped with corresponding narrowband filters, to be able to ascertain the spectral components.

A detection of aqueous proportions in the milk can be achieved by means of the blue spectral component of the light. This is preferably the case when flakes are present in the milk.

If it has been established that blood is present in the milk, it is thus suggested that cleaning of the milking system be at least partially performed. The monitoring of the cleaning is preferably performed by means of the blue spectral component of the reflected light. The cleaning can also be performed or the monitoring can also be performed when this is necessary.

If it has been established that the characteristic value exceeds a predefined reference value, the treatment of the milk can thus be decided. If the milk is milk which cannot be sold, it is thus conducted into a tank for milk which cannot be sold, whereby a clear separation is achieved between milk which can be sold and milk which cannot be sold. Additionally or alternatively, a signal can also be transmitted to the milker that the cow being milked represents a problem cow.

The calibration of the system can be performed with the aid of an animal-individual white of the milk. Alternatively, a herd-specific white can be used for the calibration. Since the animals are identified in conjunction with an upcoming milking operation, in particular by means of the known technology, in the case of an existing herd management system, which has a signal connection to the controller of the device according to the invention, it can provide items of information which can be relevant for the device. The device according to the invention can also transmit information packets to the herd management system.

Figure 4:
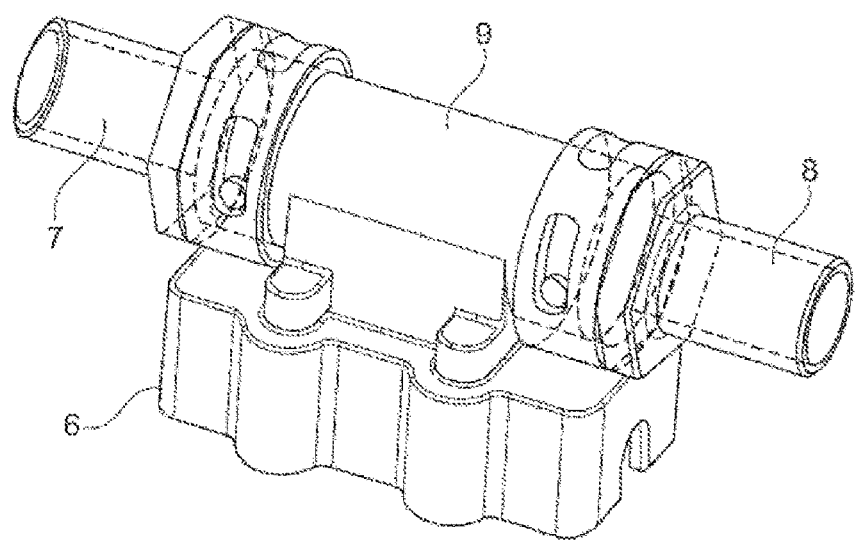
FIG. 4: schematically shows a device in a perspective view.

FIG. 4 schematically shows in a perspective view an exemplary embodiment of a device for ascertaining the quality and/or the composition of milk. The device has a housing having a bottom housing part 6 and a top housing part 9. A glass tube, which forms the chamber 1, is preferably arranged inside the top housing part 9. Connecting parts 7, 8 are connected to the top housing part 9. The connecting parts 7, 8 are connected by a bayonet joint to the top housing part 9 in the illustrated exemplary embodiment. The connecting parts 7, 8 are detachable.

Figure 5:
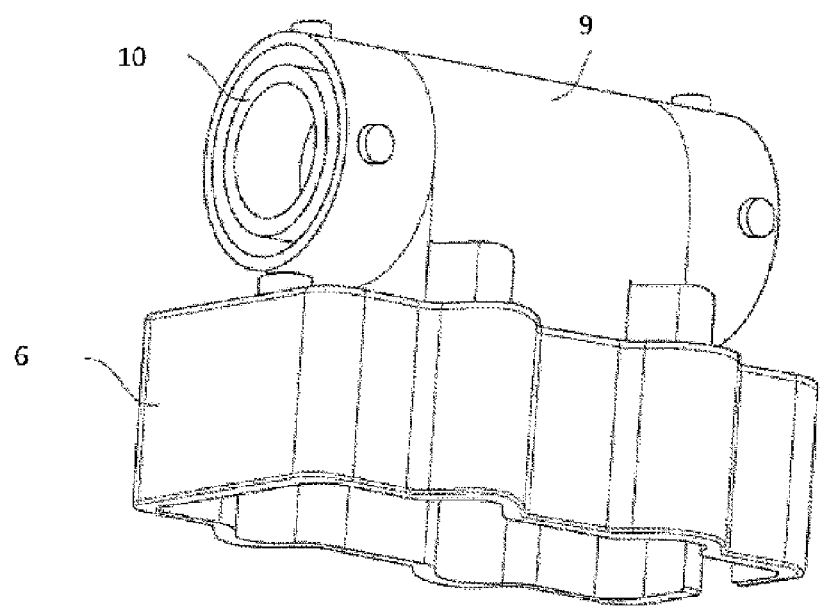
FIG. 5: schematically shows the housing of the device according to FIG. 4 in a perspective view.
Figure 6:
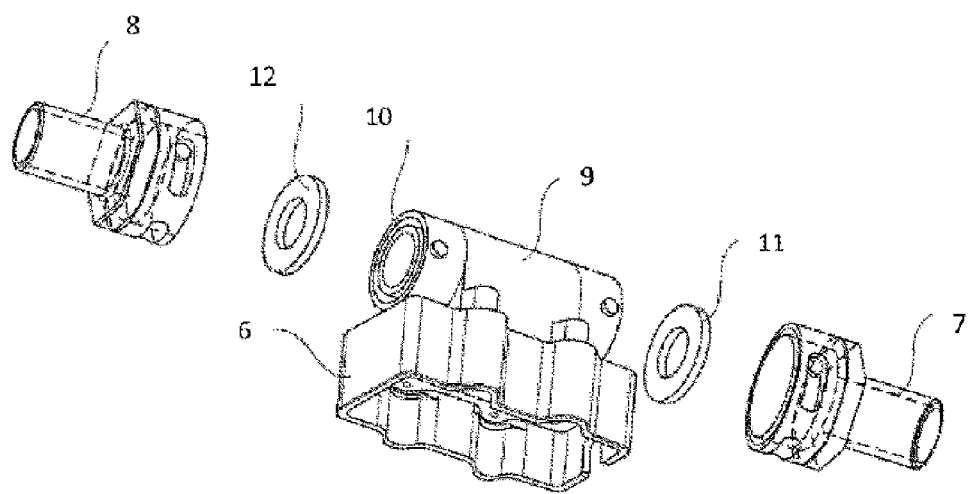
FIG. 6: schematically shows the housing of the device having connecting parts in a perspective view.

FIGS. 5 and 6 show the device having the glass tube 10, which is arranged in the top housing part 9. The top housing part 9 is implemented so that ambient light cannot enter the glass tube 10 or the chamber. Seals 11, 12 are provided for the fluid-tight connection of the connecting parts 7, 8 to the top housing part 9. The glass tube 10 is preferably glued to the top housing part 9.

Figure 7:
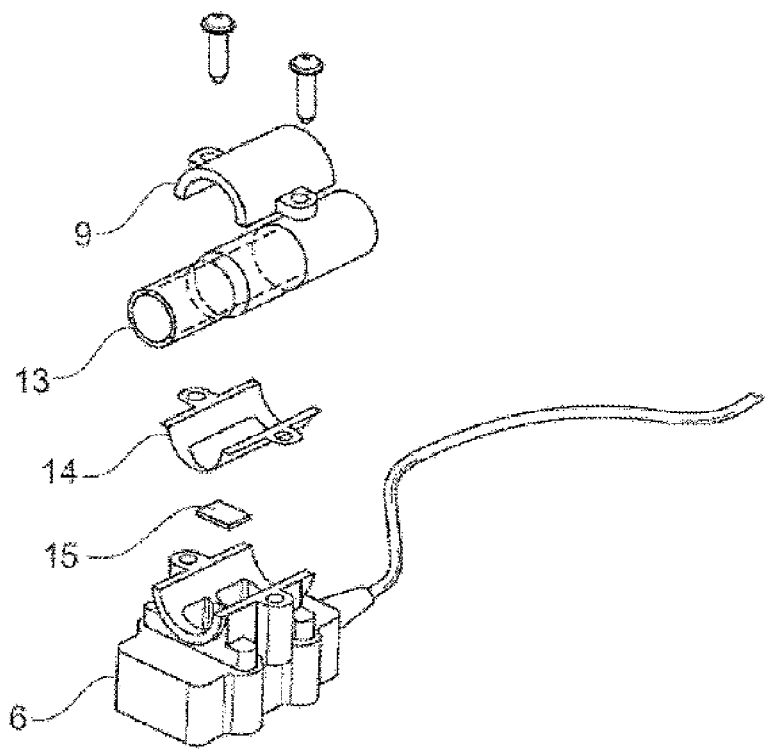
FIG. 7: schematically shows the measurement chamber of the device in a perspective view.

FIG. 7 shows a second exemplary embodiment of the device. Instead of a glass tube, a tube or line section 13 is provided. The line section 13 preferably consists of a plastic, in particular a food-compatible plastic such as, for example, PSU (polysulfone). The line section 13 is connected to the top housing part 9. A seal 14 is provided in the region of the receptacle of the line section 13. This construction of the device allows a replacement of the line section 13. An optical filter is identified with the reference sign 15.

Figure 8:
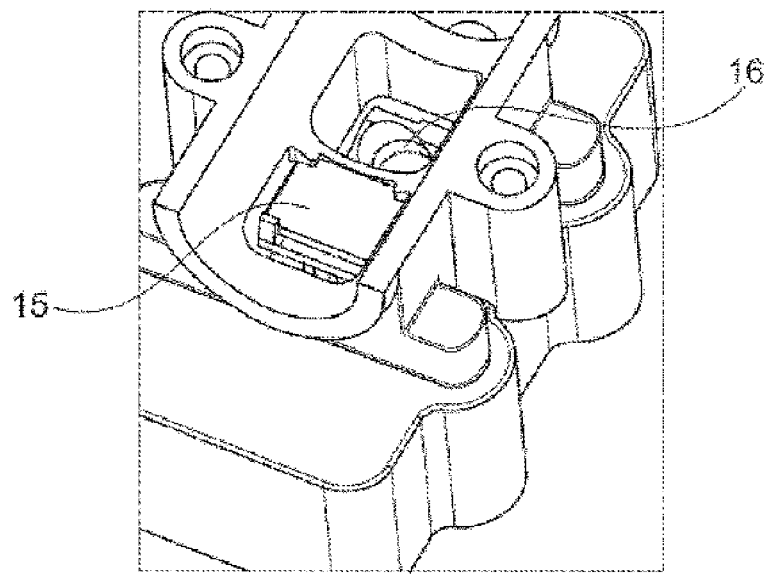
FIG. 8: shows the location of the sensor in the device.

The optical filter 15 is arranged above a receiver. FIG. 8 shows the arrangement of the filter 15. A light source 16 in the form of an LED is also shown in FIG. 8.

Figure 9:
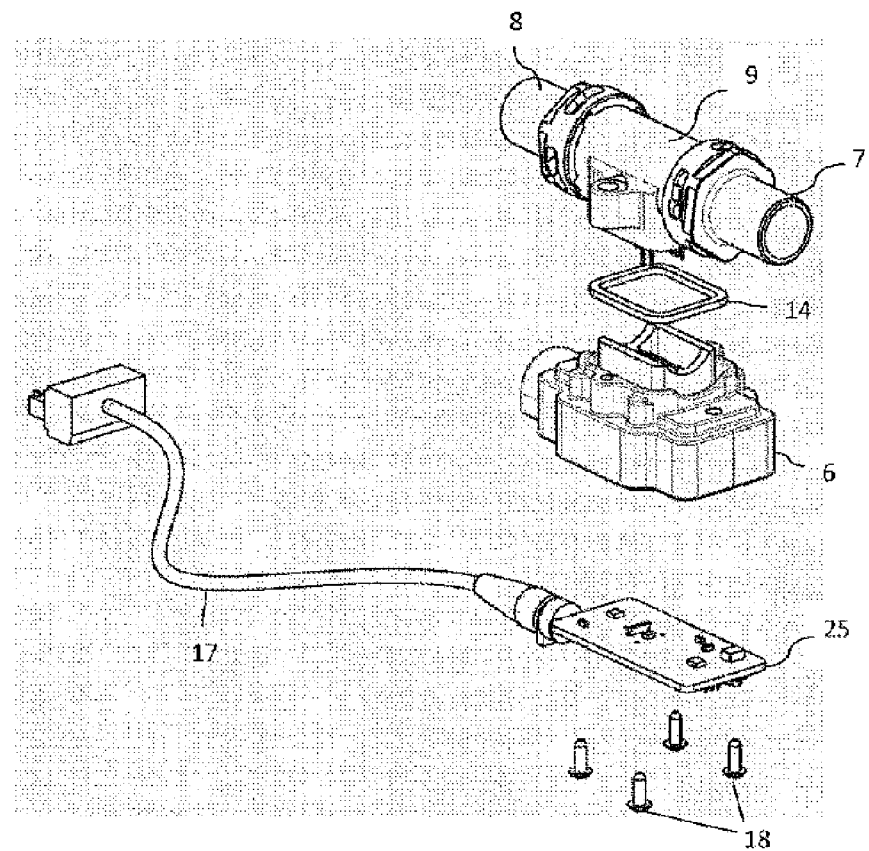
FIG. 9: schematically shows a second embodiment of the device in a perspective view.

FIG. 9 shows a perspective view of a second exemplary embodiment of a device for ascertaining the quality and/or the composition of milk. The device has a housing, which is implemented in two parts. The housing has a bottom housing part 6 and a top housing part 9. The top housing part 9 is preferably detachably connected to the bottom housing part 6. A seal 14 is arranged between the bottom housing part 6 and the top housing part 9. For example, an electronics card 25 having the corresponding electronic components is fastened by means of screws 18 in the bottom housing part 9. The electronics card 25 is connected via a signal line 17 to an analysis unit (not shown).

Figure 10:
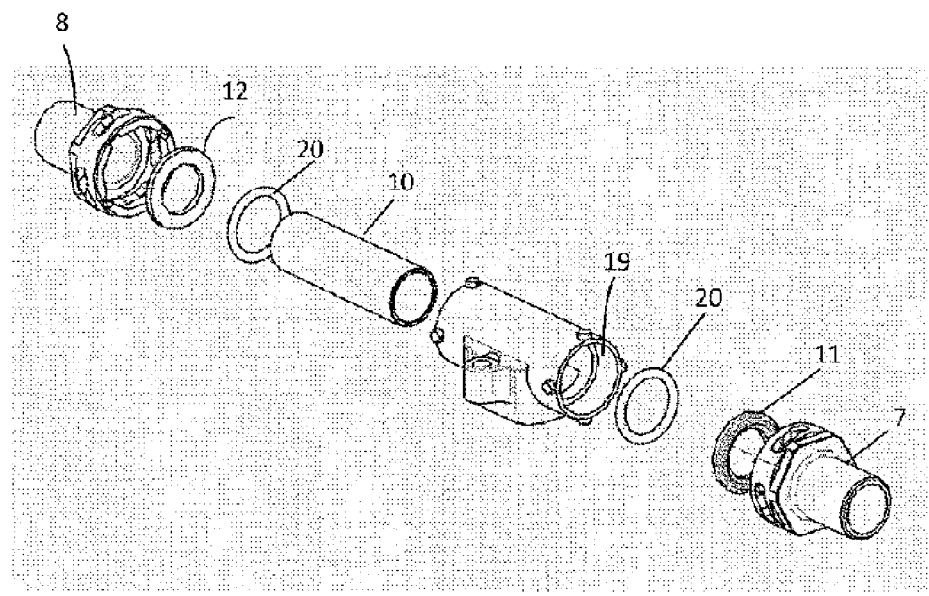
FIG. 10: shows the housing top part of the device according to FIG. 9 in a perspective view.

The top housing part 9 is schematically shown in a perspective view in FIG. 10. Connecting parts 7, 8 are detachably connected to the top housing part 9. The connection of the top housing part 9 to the connecting parts 7, 8 is implemented like a bayonet joint in the exemplary embodiment shown. In each case, a seal 11, 12 is provided between the connecting parts 7, 8 and the end face of the top housing part 9. A glass tube 10 is positioned inside the top housing part 9. Recesses 19 are provided in the respective end regions of the top housing part 9, as is apparent from FIG. 11 in particular. A seal 20 is arranged in each of the recesses 19. The seal 20 is implemented as an O-ring. The seals 20 position the glass tube 10 inside the top housing part 9. If the glass tube 10 has been arranged inside the top housing part 9 by means of the seals 20, the gap is preferably filled from the end side of the top housing part 9 using an adhesive or sealant. The seals 20 ensure that the adhesive or sealant cannot enter the inner sensor region, i.e., the region between the seals 20.

The glass tube 10 is approximately as long as the axial extension of the top housing part 9. The glass tube is thus protected from damage on its end sides. It is not necessary for a glass tube to be used. However, a glass tube is preferred, since the components of the milk, in particular water, cannot pass through the glass tube.

Figure 11:
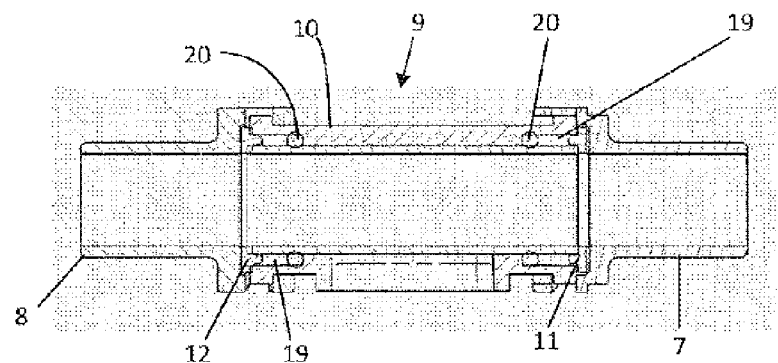
FIG. 11: shows the housing top part in section.

It is apparent from FIG. 11 that a seal 11, 12 is arranged in each case between the connecting parts 7, 8 of the top housing part 9.

Figure 12:
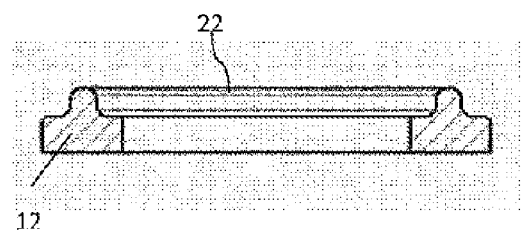
FIG. 12: shows a seal in a sectional illustration.

FIG. 12 shows the seal 12 in a section. The seal 12 is provided with a bead 22. The bead 22 engages in the gap which is formed by the glass tube 10 and the recess 19. It is ensured by this embodiment of the seal 12 that the seal 12 is not drawn into the free flow cross section by the vacuum prevailing in the glass tube. A constriction of the cross section in the transition region between the glass tube 10 and the connecting parts 7 and 8 therefore does not occur. The connecting parts 7, 8 and the seals 20 are preferably implemented so that they are light-tight. The at least one connecting part can be at least partially formed from a plastic, in particular from black PSU (polysulfone).

Figure 13:
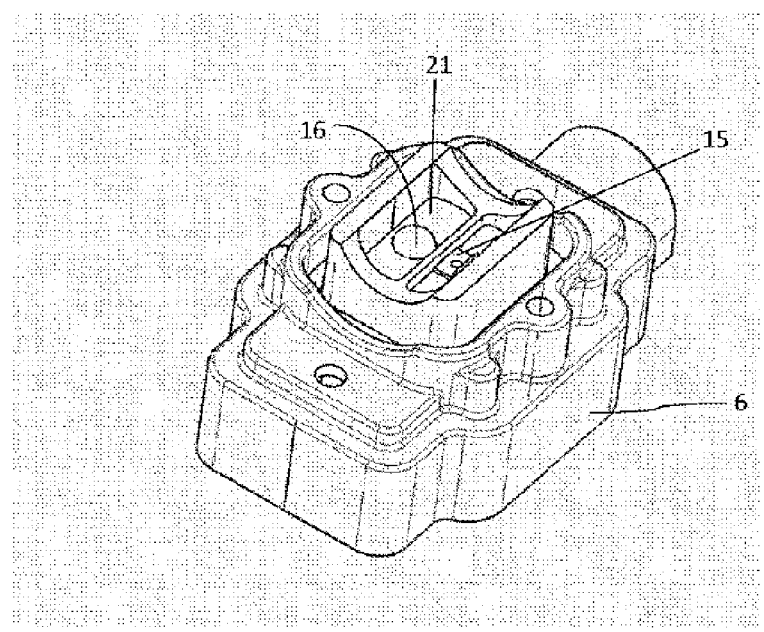
FIG. 13: shows the housing bottom part in a perspective view.

The bottom housing part 6 is shown in FIG. 13. A light source 16 and an optical filter 15 and also the further electronic components, which are not apparent from the illustration according to FIG. 13, are located in the bottom housing part 6.

The components located in the bottom housing part 6 are preferably embedded using a suitable sealant 21, so that a functioning sealing concept can be implemented inside the bottom housing part 6. Furthermore, the air volume between the light source 16 and the glass tube 10 is minimized.

During the use of the above-explained devices, the device is preferably arranged so that the glass tube 10 is positioned substantially horizontally. In the installed state, the glass tube 10 is located above the bottom housing part 6.

A calming section for the milk flow can be provided before the device. This calming section can be implemented, for example, in that the milk hose, in which the milk is supplied to the device, is laid substantially horizontally adjacent to the device.

A calibration of the device according to the invention is performed in such a manner that firstly the chamber 1 is filled up to a predefined fill level with "white" milk. The chamber 1 is preferably completely filled with white milk. The current through the light source (LED) and/or the light sources and therefore the light intensity is set so that the receiver or receivers deliver a measurement signal of predefined level in each case for the relevant wavelength of the reflected light.

After the first calibration step for the white point has been performed, a calibration of the device according to the invention is performed for at least one red point. The chamber is filled with at least one milk having a predefined known hemoglobin concentration or alternatively an amaranth concentration for this purpose. The fill level in the chamber is predefined. A measurement is now performed and the measured values thus ascertained are used for the sensor-individual scaling of the stored tables (lookup table characteristic values).

By means of this procedure, on the one hand, the intensity of the at least one light source and the sensitivity of the at least one sensor are set, and any optical tolerances and/or installation tolerances of the device according to the invention are compensated for.

Figure 14:
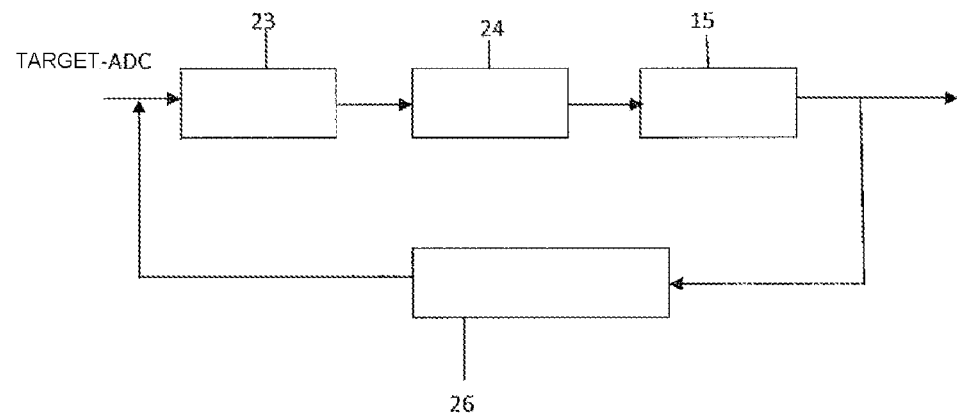
FIG. 14: schematically shows a control loop for the dynamic calibration of the color sensor.
Figure 15:
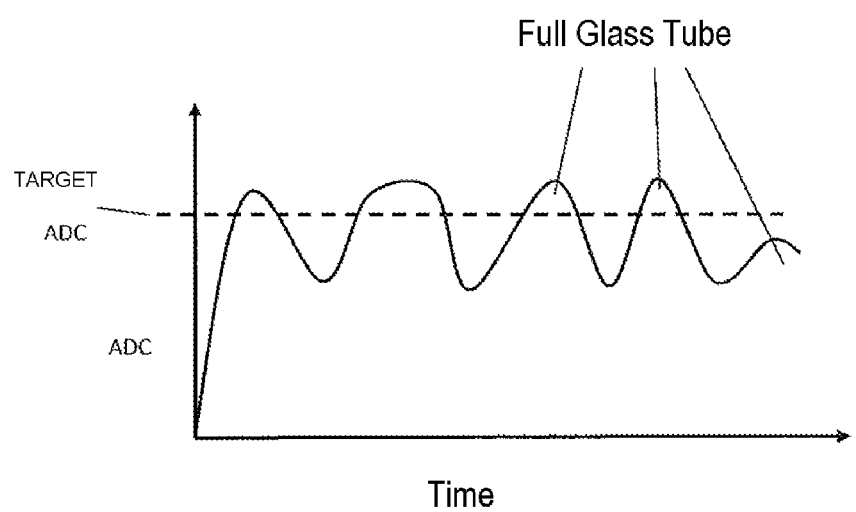
FIG. 15: schematically shows a typical course of the ADC signal for a color channel.
Figure 16:
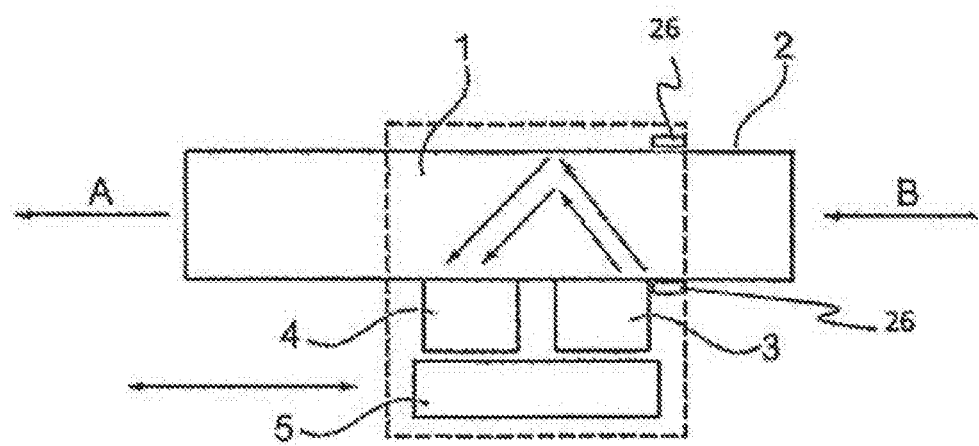

The light source which is used inside the device is also subject to aging influences, so that milk/white differences can arise. The milk/white differences can also be herd-individual or animal-individual. A white ADC value (white analog-digital converter value) measured by the device can be influenced in operation by the reference white, for example, by aging of the light source, the feed type, or the fat content of the milk. A control loop, as shown in FIG. 14, is proposed for the dynamic calibration. The control loop has a regulator 23, a power source 24, and a light source 16 of the color sensor. The calibration of the device is performed when the glass tube 10 is filled with a white liquid. A continuous acquisition of the reflected light intensity is performed by means of the device. A typical signal course is shown in FIG. 15. The milk flow during a milking operation is not necessarily periodic, but rather pulsed, as can be inferred from FIG. 15. The fuller the glass tube 10 is filled, the more light is acquired by the device. According to the illustration of FIG. 15, a periodic nature of the saturation signal is visible. This saturation corresponds to the point in time at which the glass tube is completely filled with milk. A deviation from the ADC signal from the target ADC white signal is determined by averaging. The regulator 23 receives a regulation deviation and controls the power source 24 of the light source 16 of the color sensor until the regulation deviation is less than a minimal deviation. The ADC signal is a digital signal which was obtained from an analog signal. This is performed by means of a corresponding converter (analog-digital converter).

The invention claimed is:

1. A method for ascertaining the quality and/or the composition of milk during a milking operation, the method comprising the steps of:
    allowing milk to flow through a milk hose flow-through chamber in a milk line without redirecting the milk flow through a milk phase separation device or extracting only a predetermined volume of single-phase milk for testing;
    determining a fill level of the milk in a milk hose flow-through chamber as the milk volume flowing through the milk hose flow-through chamber;
    irradiating the milk in the flow-through chamber using at least one radiation of a predefined wavelength to create a reflected radiation;
    measuring an intensity of the reflected radiation;
    generating a value pair of a fill level and the intensity of the reflected radiation;
    ascertaining a characteristic value associated with the value pair from stored characteristic values; and
    comparing the ascertained characteristic value to a reference value to determine a characteristic about the milk, wherein the characteristic is selected from the group consisting of:
        a quality of the milk, and the composition of the milk, or combinations thereof.

2. The method of claim 1, wherein the step of irradiating the milk includes using red light to irradiate the milk and the step of determining the fill level of the milk is determined at least in part from the intensity of the reflected red light.

3. The method of claim 1, wherein the predefined wavelength corresponds to a wavelength of light selected from the group consisting of: green light, blue light, and a combination of both green light and blue light.

4. The method of claim 2, wherein the step of irradiating the milk includes the steps of successively or simultaneously using a light from the group consisting of: red light, green light, blue light, and combinations thereof.

5. The method of claim 1, wherein the step of irradiating the milk includes the step of applying pulsing radiation.

6. The method of claim 1, and further comprising the step of:
storing the characteristic values in the form of a table.

7. The method of claim 1, and further comprising the step of:
determining a characteristic value from the fill level and the intensity of the reflected radiation as parameters in a mathematical relationship.

8. The method of claim 1, wherein the step of determining the fill level comprises the step of:
detecting a milk stream.

9. The method of claim 1, wherein the radiation is a monochromatic radiation.

10. The method of claim 1, wherein the fill level is determined capacitively.

11. The method of claim 1, wherein the fill level in the chamber is predefined.

12. The method of claim 1, and further comprising the steps of:
providing at least one sensor having at least one light source and at least one receiver, wherein the sensor is calibrated to a herd-specific white of the milk.

13. The method of claim 1, and further comprising the steps of:
providing a sensor that has a light source which emits red light and a receiver which receives red light, and
calibrating the sensor with a predefined red liquid.

14. The method of claim 1, wherein milked milk flows through the chamber.

15. The method of claim 1, and further comprising the step of:
successively ascertaining multiple characteristic values during a milking operation.

16. The method of claim 1, and further comprising the step of:
conducting the milk into a tank for milk which can be used or milk which cannot be used in dependence on at least one characteristic value.

17. The method of claim 1, wherein the step of determining the fill level comprises the step of:
detecting a minimum milk stream.

18. The method of claim 1, wherein the fill level is determined inductively.

19. The method of claim 1, and further comprising the steps of:
providing at least one sensor having at least one light source and at least one receiver, wherein the sensor is calibrated to an animal-individual white of the milk.

20. A method for ascertaining the quality and/or the composition of milk during a milking operation, comprising the steps of:
allowing milk to flow through a milk hose flow-through chamber in a milk line without redirecting the milk flow through a milk phase separation device or extracting only a predetermined volume of single-phase milk for testing;
measuring a height of a fill level of the milk in a chamber as the milk volume flowing through the chamber;
irradiating the milk flowing through the chamber using at least one radiation of a predefined wavelength;
measuring an intensity of the reflected radiation;
ascertaining a characteristic value associated with a value pair of a height of the fill level and an intensity of the reflected radiation from stored characteristic values; and
comparing the ascertained characteristic value to a reference value to determine a characteristic about the milk.

21. The method of claim 20, wherein the step of measuring the height of the fill level comprises the steps of:
irradiating the milk flowing through the chamber using red light;
determining the height of the fill level from the intensity of the red light reflected from the milk in the chamber.

22. The method of claim 20, wherein the predefined wavelength corresponds to a wavelength from the group consisting essentially of: green light, blue light, and combinations of green light and blue light.

23. The method of claim 20, wherein the chamber is formed by a section of a milk hose, wherein during the milking operation the milk flows through said section of the milk hose forming said chamber.

24. The method of claim 20, wherein the chamber is formed by a section of a line system of a milking system, so that the quality and/or the composition of the milk is/are already ascertained during the milking operation.

25. The method of claim 20, wherein the height of the fill level and the intensity of the reflected radiation are measured at the same point in time so as to form the value pair.

26. The method of claim 1, wherein the characteristic about the milk is a characteristic about the composition of the milk.

27. The method of claim 1, wherein the characteristic about the milk is a characteristic about the quality of the milk.

28. The method of claim 20, wherein the characteristic about the milk is a characteristic about the composition of the milk.

29. The method of claim 20, wherein the characteristic about the milk is a characteristic about the quality of the milk.

* * * * *